United States Patent [19]
Unger et al.

[11] Patent Number: 5,977,538
[45] Date of Patent: Nov. 2, 1999

[54] OPTOACOUSTIC IMAGING SYSTEM

[75] Inventors: Evan C. Unger; Yunqiu Wu, both of Tucson, Ariz.

[73] Assignee: Imarx Pharmaceutical Corp., Tucson, Ariz.

[21] Appl. No.: 09/075,567

[22] Filed: May 11, 1998

[51] Int. Cl.[6] .............................. A61B 8/00; G01S 15/02; G01N 29/00; H04N 5/30

[52] U.S. Cl. .......................... 250/227.2; 73/601; 73/620; 73/625; 73/628; 73/632; 73/866.5; 348/163; 367/7; 367/137; 600/310; 600/443; 600/446

[58] Field of Search ........................... 250/227.11, 227.2, 250/227.21, 227.26; 73/596, 601, 603, 605, 606, 618, 620, 624, 625, 626, 627, 628, 629, 632, 641, 642, 866.1, 866.5; 348/163; 367/7, 137, 138, 191; 600/109, 310, 437, 440, 443, 446, 476

[56] References Cited

U.S. PATENT DOCUMENTS

| | | | |
|---|---|---|---|
| 3,790,281 | 2/1974 | Kessler et al. | 356/72 |
| 4,011,748 | 3/1977 | Bond et al. | 73/601 |
| 4,518,992 | 5/1985 | Kessler et al. | 348/163 |
| 4,611,493 | 9/1986 | Muth | 73/606 |
| 4,869,256 | 9/1989 | Kanno et al. | 600/440 |
| 4,993,416 | 2/1991 | Ophir | 600/442 |
| 5,840,023 | 11/1998 | Oraevsky et al. | 600/407 |

OTHER PUBLICATIONS

Fatemi and Greenleaf, "Ultrasound–Simulated Vibro–Acoustic Spectrography," Science, vol. 280, pp. 82–85, Apr. 3, 1998.

*Primary Examiner*—John R. Lee
*Attorney, Agent, or Firm*—Woodcock Washburn Kurtz Mackiewicz & Norris LLP

[57] ABSTRACT

An optoacoustic system comprises an optoacoustic transducer including a first array of acoustic transducers and a second array of optical fibers; an acoustic subsystem for controllably exciting at least a first subset of the acoustic transducers to generate acoustic pulses with a prescribed pulse width, and for forming a first image based on return acoustic pulses reflected from a patient; an optical subsystem for controllably generating optical pulses to be transmitted through at least a first subset of the optical fibers toward the patient, and for forming a second image based on light reflected from the patient; and image correlation means for correlating the first and second images. The first and second arrays may take various forms, including the form of an annular array in which the acoustic transducers are arranged coaxially and the optical fibers are disposed around an outer periphery of the first array. The first and second arrays may also take the form of linear arrays.

34 Claims, 4 Drawing Sheets

FIG.4A
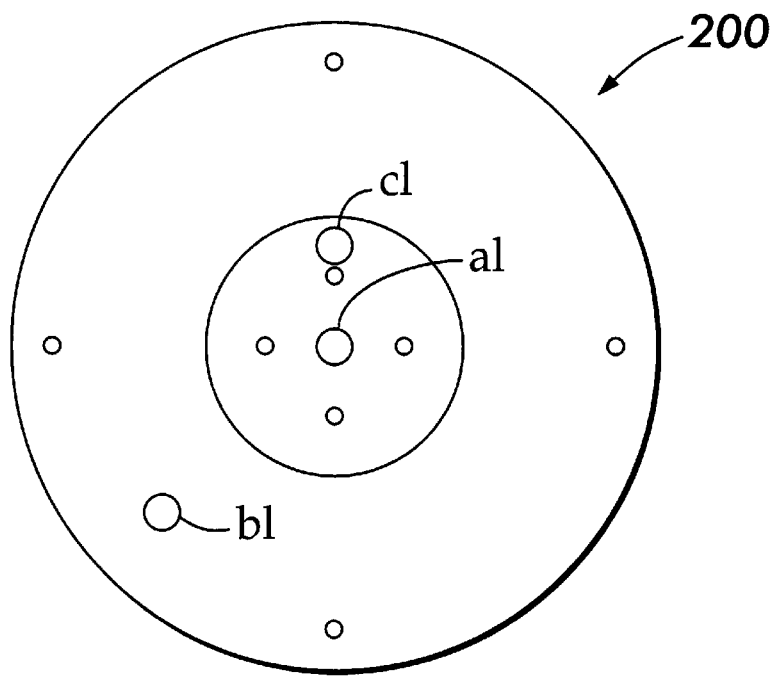
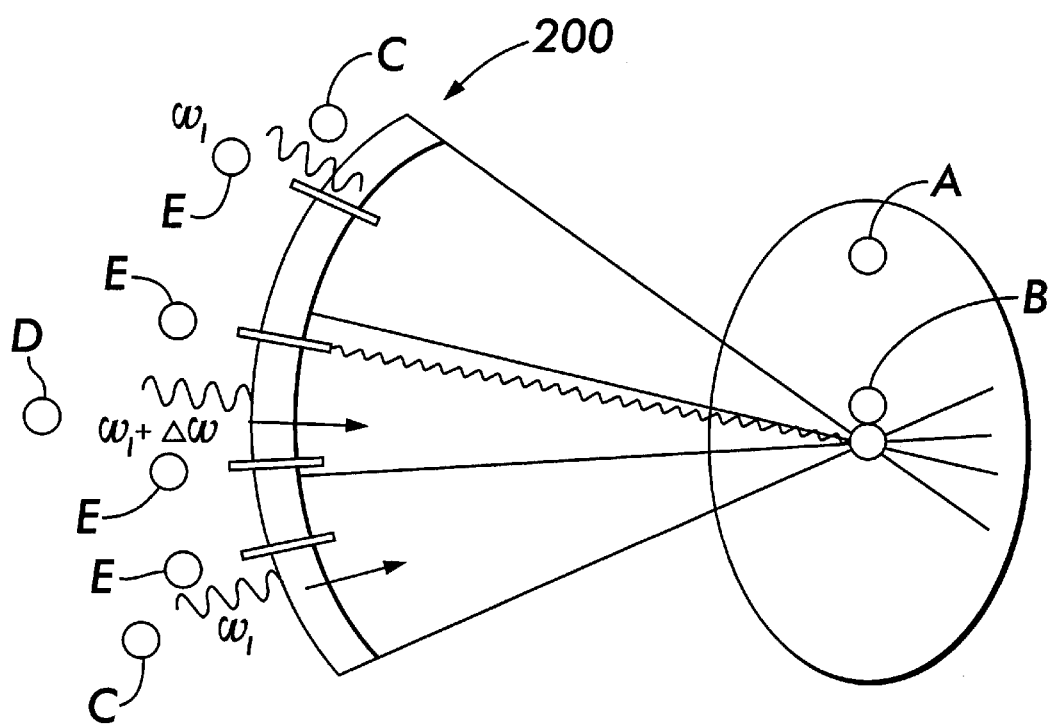
FIG.4B

OPTOACOUSTIC IMAGING SYSTEM

FIELD OF THE INVENTION

The present invention relates generally to optoacoustic systems and methods, and more particularly to optoacoustic imaging systems and methods for performing diagnostic and therapeutic imaging.

BACKGROUND OF THE INVENTION

Optical and acoustic (e.g., ultrasound) imaging have each been used as separate modalities for diagnostic imaging. Each of these modalities has limitations owing to the physics involved.

For example, while ultrasonic energy used for imaging can have very good penetration, e.g., it can penetrate through up to 20 centimeters of tissue without much signal attenuation, the available resolution depends upon the spatial pulse length used. For example, one cycle of a pulse of a 5 MHz signal will provide a resolution of about 0.3 millimeters. (This estimate is based on a propagation speed of 1.5 mm/$\mu$s; i.e., one cycle=0.2 $\mu$s×1.5 mm/$\mu$s=0.3 mm.) In other words, with a frequency of 5 MHz, one can not detect anything smaller than 0.3 millimeters or differentiate two features with a separation of less than 0.3 millimeters.

Optical energy, on the other hand, offers good resolution but very limited penetration, due to attenuation and scattering of light in tissue. The resolution possible with optical imaging is based on the wavelength of the light. Typical optical imaging wavelengths are in the micrometer range, and therefore resolutions on the order of micrometers are possible. Moreover, since tissues with different metabolisms (such as cancerous tissues) often exhibit different optical absorption characteristics, different optical wavelengths may be advantageously employed for imaging and detection of abnormal tissue.

Thus, optical imaging is hampered by relatively poor penetrability and difflusion, and ultrasound imaging is hampered by its relatively poor spatial and contrast resolution for defining the physiology of images. These modalities may be combined, however, to provide new and improved systems and methods for imaging. Copending U.S. patent application Ser. No. 08/993,165, filed Dec. 18, 1997, entitled "Optoacoustic Contrast Agents and Methods for Their Use," which is hereby incorporated by reference in its entirety, discloses novel optoacoustic contrast agents and methods of imaging using such contrast agents. The present invention was made during the process of designing an imaging system and associated optoacoustic transducer for use, preferably, with the novel contrast agents.

SUMMARY OF THE INVENTION

The present invention combines optical and acoustic imaging techniques to achieve improved penetration as well as improved resolution. In addition, the invention provides a mechanism to obtain information not available by way of either optical or acoustic imaging alone. For example, the "optical image" (the image obtained by optics) provides superficial functional information concerning, e.g., metabolic status or oxygen cycle of an area of tissue, but not its physical structure. The "ultrasonic image" (the image obtained by acoustics) provides the structural information but not the metabolic information.

Thus, for example, an ultrasonic breast image obtained by the present invention could depict the whole breast but not the fine detail of a lump, whereas a corresponding optical image could show that a small area, the lump, has a metabolism which is different from that of the surrounding normal tissue. By correlating the two images, or superimposing one upon the other, the present invention permits the physician to accurately and precisely locate the lump.

In a presently preferred embodiment, an optoacoustic system in accordance with the present invention comprises an optoacoustic transducer including a first array of acoustic transducers and a second array of optical fibers; acoustic system means for controllably exciting at least a first subset of the acoustic transducers to generate acoustic pulses with a prescribed pulse width, and for forming a first image based on return acoustic pulses reflected from a patient; optical system means for controllably generating optical pulses to be transmitted through at least a first subset of the optical fibers toward the patient, and for forming a second image based on light reflected from the patient; and image correlation means for correlating the first and second images. As used herein, to correlate the optically and acoustically generated images means to superimpose or align one with the other such that the viewer (physician or other health care worker) will be able to identify where an abnormality is located with respect to the entire structure being examined.

In accordance with the present invention, the same acoustic transducers may be used to both transmit and receive acoustic pulses to and from the patient. Alternatively, different subsets, or subarrays, of the acoustic transducers may be used to transmit and receive the acoustic pulses to/from the patient. Moreover, the first array preferably comprises a plurality of ultrasonic transducers, and more specifically piezoelectric transducers.

The first and second arrays may take various forms. For example, in one preferred embodiment, the first array is an annular array in which the acoustic transducers are arranged coaxially and the second array comprises a circular array of optical fibers disposed around an outer periphery of the first array. Alternatively, the second array may be disposed around an inner periphery of the first array. The second array may also include a bundle of optical fibers disposed within the inner periphery.

In another form of the invention, the first and second arrays are linear arrays mutually arranged as shown in the drawings and described below.

In preferred embodiments of the invention, the optical system means comprises means for generating pulses of light of a plurality of wavelengths. As disclosed below, this permits the system to be used to distinguish tissues having different absorption characteristics (or image features thereof) from one another. In addition, to produce the plurality of wavelengths, the optical system may include multiple lasers or, alternatively, a single white light source and a chopper.

Further, the inventive system may also include means for simultaneously exciting groups of at least two of the acoustic transducers, and preferably means for sequentially exciting different groups of the acoustic transducers. This type of "scanning" may be employed to improve the spatial resolution of the acoustic image.

In addition, in preferred embodiments of the invention, the optical system means comprises a picosecond pulser for generating optical pulses having a pulse width preferably in the range of 0.01 picosecond to 100 nanoseconds, and most preferably in the range of about 0.1 picosecond to 10 nanoseconds.

The system may also advantageously include means for providing a beam reference and trigger signal ($LS_1'$) indicative of the timing of the optical pulses transmitted through the first subset of the optical fibers toward the patient.

Other features and advantages of the invention are disclosed below.

BRIEF DESCRIPTION OF THE DRAWINGS

FIGS. 4A and 4B schematically depict an embodiment of the present invention employing a confocal optoacoustic transducer.

DETAILED DESCRIPTION OF PREFERRED EMBODIMENTS

Figure 1:
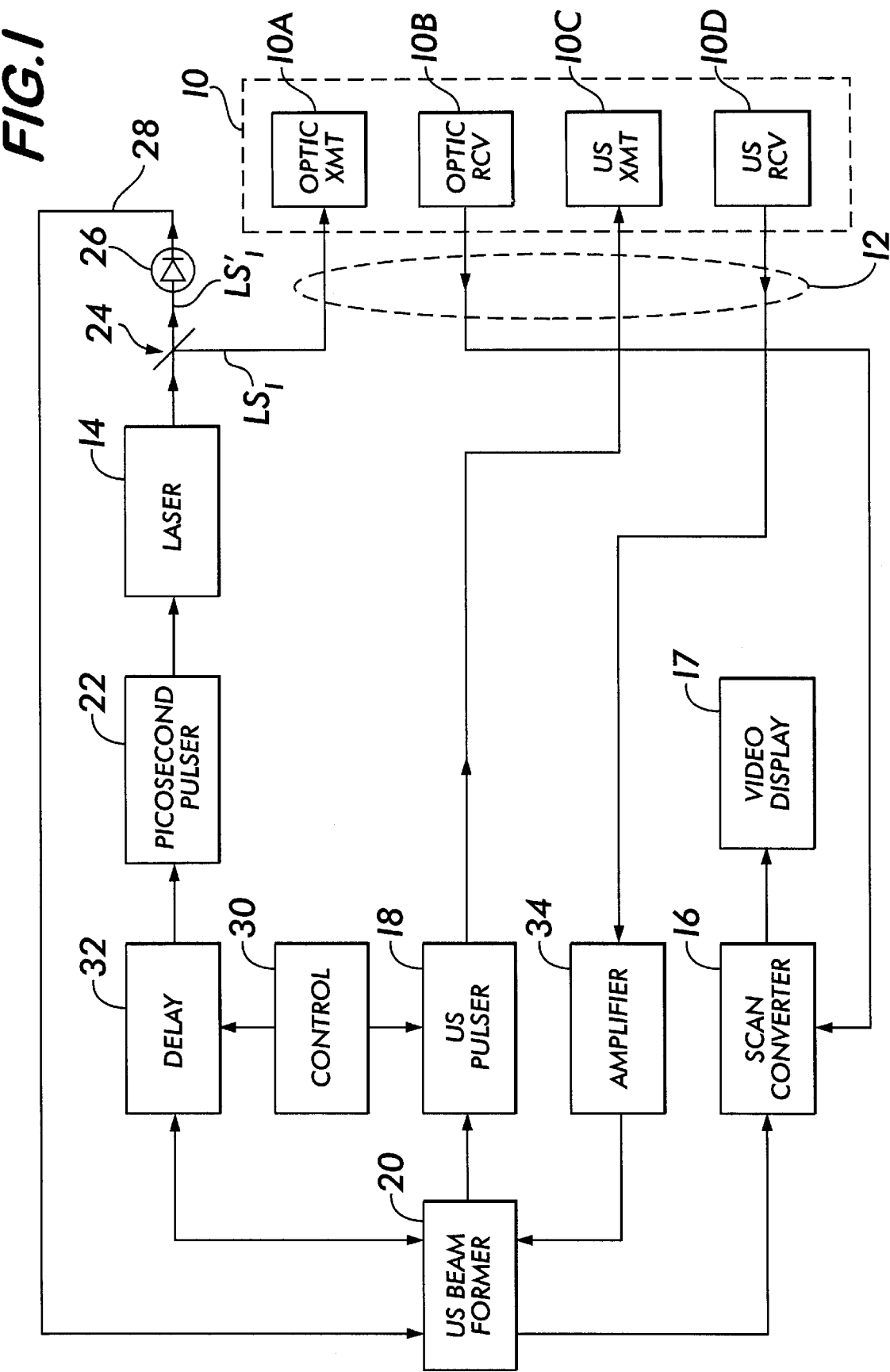
FIG. 1 is a block diagram of a presently preferred embodiment of an optoacoustic imaging system in accordance with the present invention.

As shown in FIG. 1, a presently preferred embodiment of the invention comprises an optoacoustic transducer 10 made up of a plurality of arrays of transmit and receive elements. For example, the system may include an optical transmit array 10A, an optical receive array 10B, an ultrasound transmit array 10C and an ultrasound receive array 10D. Various configurations for these arrays are discussed below and depicted in FIGS. 3A–3F. The system of FIG. 1 also includes a cable 12 for carrying optical and electrical energy, or signals, to and from the optical and ultrasound arrays, respectively. As will be clear from the following discussion, the optical transmit array 10A receives optical energy from a laser 14 (or other suitable light source), and the optical receive array 10B provides received optical energy to a scan converter 16. The scan converter 16 contains the memory and software needed to drive a video display 17. The elements making up the transmit and receive ultrasound arrays 10C and 10D convert electrical energy to acoustic energy, and vice versa. Thus, the ultrasound transmit array 10C receives electrical pulses from an ultrasound pulser 18 and converts the electrical pulses to acoustic pulses. The ultrasound receive array 10D receives acoustic pulses reflected from the patient and converts these to electrical pulses, and then provides these electrical pulses to a beamformer 20.

The inventive system of FIG. 1 further includes a picosecond pulser 22, a beam splitter 24 for dividing the laser output into a main signal $LS_1$ and a secondary signal $LS_1'$; a transducer 26 for converting the secondary signal $LS_1'$ into an electrical beam reference and trigger signal; and a signal path 28 for providing the electrical beam reference and trigger signal $LS_1'$ to the beamformer 20. The beam reference and trigger signal $LS_1'$ enables the system to properly correlate, or combine, the separate ultrasonic and optical images obtained by the system. In addition, a controller 30 is coupled to a delay unit 32, which is further coupled to the ultrasound beamformer 20 as well as to the picosecond pulser 22, and to the ultrasound pulser 18. As shown, an amplifier 34 is used to amplify the received ultrasound energy, after conversion to electrical pulses, and the amplified pulses are fed to the beamformer 20. The amplifier 34 may also perform filtering algorithms, as necessary. The beamformer 20 is coupled to the scan converter 16, which is in turn coupled to a video display 36.

The picosecond pulser 22 may be purchased as an off-the-shelf component or may be constructed on a custom circuit board. Its essential function is to output an electrical pulse with a pulse width (or duration) on the order of a picosecond. This is important because, as mentioned above, the resolution of an optical signal depends upon both the wavelength and the pulse width of the signal. Moreover, although shorter pulse widths may be possible, the present inventors have found that a pulse width on the order of a picosecond is sufficient and provides an economically feasible solution in view of the significantly more expensive circuitry required to obtain pulses of less than a picosecond.

The controller 24 controls the generation of optical pulses by the laser 14 by way of triggering the picosecond pulser 14. The controller 24 also controls the generation of ultrasound pulses by triggering the ultrasound pulser 30.

It should be noted that most of the components depicted in FIG. 1 are part of a typical ultrasound scanner. The key components for ultrasonic scanners include a pulser, a receiver, a beamformer, a scan converter, as well as a display.

After the laser 16 is triggered, the light generated by the laser is split by the beam splitter 18 and transmitted via the array 10A to the patient. The detector array 10B senses the optical response signal from the patient and provides a signal indicative thereof to the scan converter 34. Because it is important to know how much light was transmitted to the patient, the signal $LS_1'$ on line 22 serves as both a trigger and as a reference. The trigger provides the timing information necessary to ascertain the distance between two features of the image, and thus allows the optical image to be correlated with the ultrasonic image.

Figure 2A:
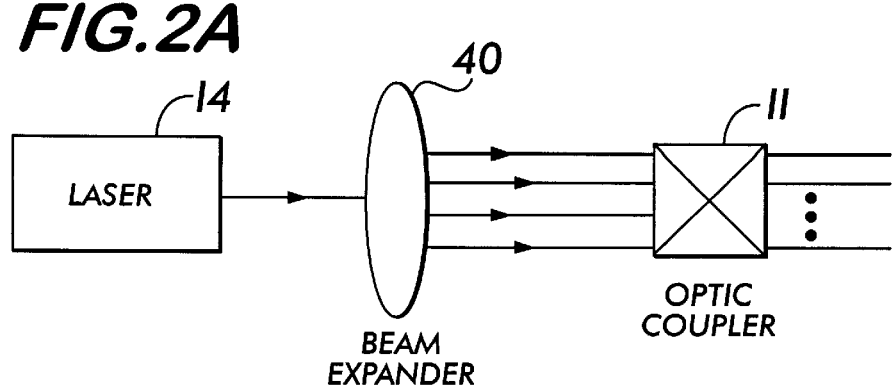
FIGS. 2A through 2C schematically depict alternative arrangements for coupling optical energy from a laser or other light source to a fiber optic coupler.
Figure 2B:
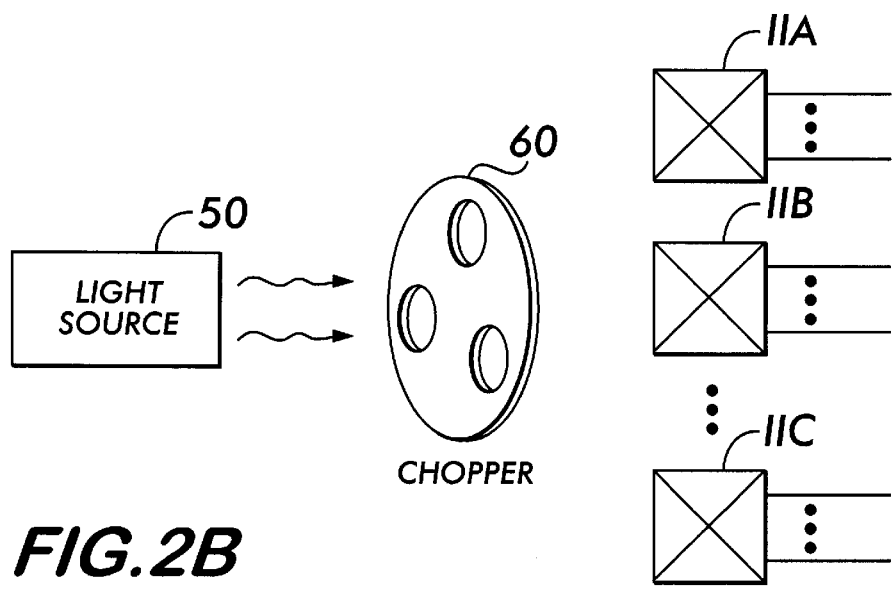
Figure 2C:
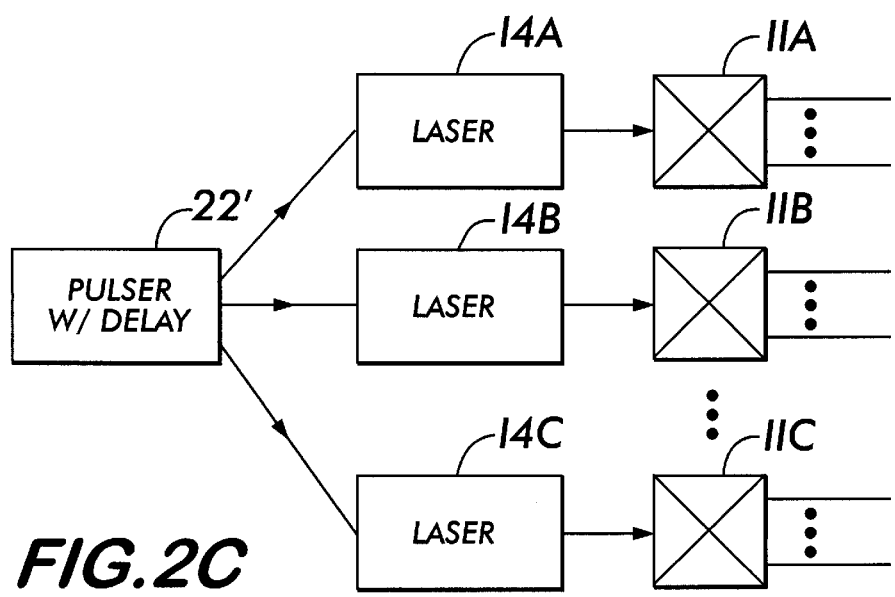

As mentioned, FIGS. 2A through 2C depict alternative arrangements for coupling optical energy from a laser(s) or other light source to a fiber optic coupler. Referring to FIG. 2A, a laser 16 outputting a single wavelength or a narrow band of wavelengths may be used in conjunction with a beam expander 40 and an optic coupler 11. The coupler 11 feeds the optical signal from the laser 16 to a plurality of optical fibers.

As shown in FIG. 2B, in accordance with another embodiment of the invention, a white light source 50 may be used in conjunction with a chopper 60 to generate a plurality of wavelengths (or bands of wavelengths), which are in turn coupled to a plurality of optic couplers 11A, 11B, 11C, etc., each of which feeds the optical energy to a plurality of optical fibers.

As shown in FIG. 2C, a third example employs a pulser 22' having built-in delay to trigger a plurality of lasers 14A, 14B, 14C, etc., each of which outputs optical energy of a different wavelength or band of wavelengths.

As mentioned above, the use of different wavelengths may be important since different kinds of tissues may have different absorption characteristics. For example, hemoglobin has a different light absorption characteristic than oxyhemoglobin. Therefore, by imaging with different wavelengths of light, the system is able to ascertain, by calculation, the percentage of hemoglobin and the percentage of oxyhemoglobin. Similarly, the tissue making up a tumor will typically have a metabolic rate different from that of normal tissue, and therefore will be detectable with different wavelengths of light.

Figure 3A:
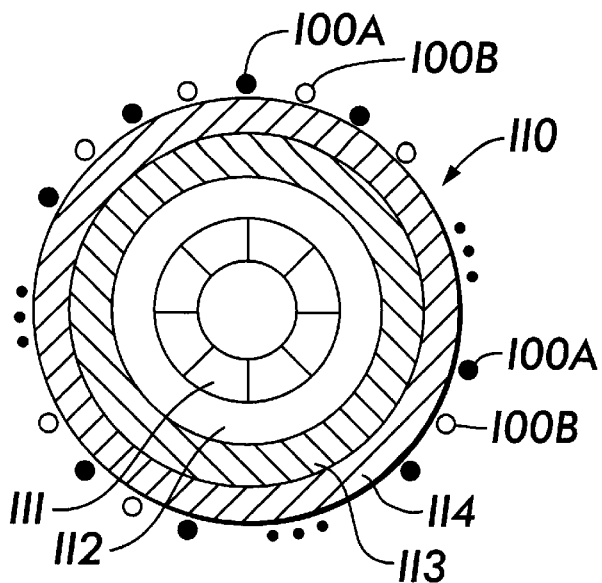
FIGS. 3A through 3F schematically depict alternative embodiments of an optoacoustic transducer in accordance with the present invention.
Figure 3B:
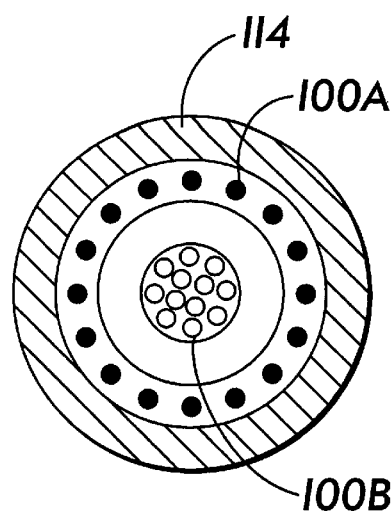
Figure 3C:
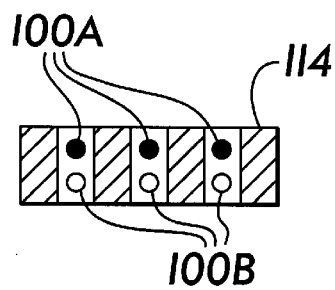

Various embodiments of optoacoustic transducers in accordance with the present invention are depicted in FIGS. 3A through 3F. FIGS. 3A and 3B depict annular optoacoustic arrays; and FIGS. 3C–3F depict linear optoacoustic arrays.

Before discussing the various configurations depicted in FIGS. 3A–3F in greater detail, it should be noted that the ultrasound elements of the transducer will preferably comprise piezoelectric elements (film or ceramic) supported by a metallic substrate (or backing layer). In addition, an impedance matching layer will typically be placed on the side opposite the substrate. The matching layer is designed to efficiently couple the acoustic energy from the piezoelectric elements to the medium (typically air) through which the energy will be transmitted to the patient. Moreover, although it is possible not to use a backing layer, in which case the piezoelectric elements would be air-backed, this is not preferred since such air backed transducers typically exhibit very long resonance and thus are not able to achieve a very short pulse width.

Referring now to FIG. 3A, a first embodiment of the optoacoustic transducer comprises a first array 110 of piezoelectric transducers, denoted 111, 112, 113 and 114, and a second array of optical fibers, including fibers 100A used for transmitting optical pulses toward the patient and fibers 100B used for carrying received pulses to the scan converter 16 (FIG. 1). In the embodiment of FIG. 3A, all of the optical fibers are disposed in a circular array around the periphery of the ultrasound array 110.

Alternatively, as shown in FIG. 3B, the transmit optical fibers 100A may be disposed in a circular array within the outenmost piezoelectric layer 114, and the receiving optical fibers 100B may be placed within a central portion of the transducer, along its longitudinal axis.

Figure 3D:
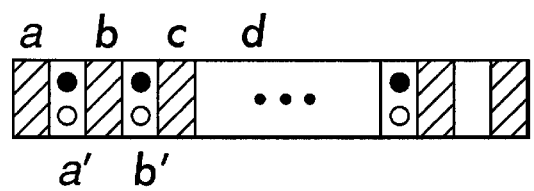

In the embodiment shown in FIG. 3D, the ultrasonic and optical elements are configured in a linear array. In the embodiment depicted in FIG. 3D, the respective ultrasonic elements, which are indicated by unprimed letters a, b and c, and the respective optical elements, indicated by the primed letters a' and b', are excited in groups, e.g., two at a time. This improves the lateral spatial resolution of the images produced by the system. For example, the piezoelectric element a and the neighboring element b are excited, or pulsed, simultaneously, and then elements b and c are excited simultaneously, and then elements c and d, and so forth. Moreover, optical elements a', b', etc., can carry the same wavelength of light or different wavelengths.

Figure 3E:
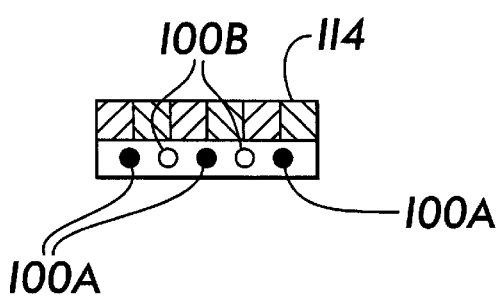
Figure 3F:
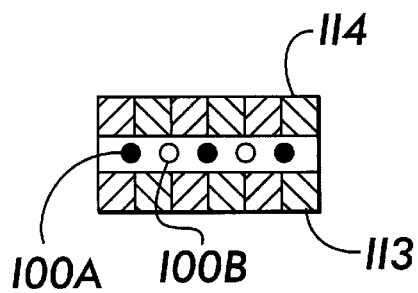

FIGS. 3E and 3F depict other possible configurations of the acoustic and optical elements.

An optoacoustic imaging system of the kind disclosed herein can be used for diagnostic imaging of patients with intracranial gliomas to localized tumors, to identify tumor remaining at the resection margins, and to determnine the grade of the tumor. For example, the patient may undergo surgery for the removal of an intrinsic brain tumor. A contrast agent of the kind disclosed in the above-cited application Ser. No. 08/993,165, containing microbubbles and/or dyes (such as indocyanine green) may be injected into the patient intravenously. The composite images (ultrasonic and optical, pre- and post-contrast) may be employed to differentiate between remaining tumor tissue and normal brain tissue. Such real-time information helps the surgeon to maximize tumor resection while sparing normal brain tissue and increasing the diagnostic accuracy and safety of the procedure.

The present invention is not limited to the specific, presently preferred embodiments disclosed above. For example, as shown in FIGS. 4A and 4B, the present invention may be implemented by employing a confocal optoacoustic transducer 200 operating with two different frequencies of sound. In FIG. 4A, reference character "a1" represents a central transducer element with a frequency= $\omega_1+\Delta\omega$; reference character "b1" represents peripheral elements with frequency=$\omega_1$; and reference character "c1" represents fiber optic laser sources. Both the source fibers and crystal face may be designed to receive optical signals. In FIG. 4B, reference character "A" represents the object to be analyzed; reference character "B" represents the focal zone of the ultrasonic beam; reference character "C" represents the crystal face of the confocal transducer 200 with frequency of sound=$\omega_1$; reference character "D" represents the central crystal face of the confocal transducer with the frequency of sound=$\omega_1+\Delta\omega$; and reference character "E" represents the fiber optic laser sources. One laser is fired to intersect the focal zone "B" of the ultrasound. The interaction of the two ultrasound sources, with frequencies of $f_1=\omega 1$ and $f_2=\omega_1+\Delta\omega$, at the focal zone "B" results in additive waveforms to create a stronger acoustic mirror and to thereby improve the reflection of sound. For further background information regarding the use of confocal transducers, see M. Fatemi, et al., *Ultrasound-Stimulated Vibro-Acoustic Spectrography*, Science Vol 280, Apr. 3, 1998.

Accordingly, except as they may be specifically so limited, the scope of the protection of the following claims is not limited to the presently preferred embodiments disclosed herein, but rather is intended to cover all obvious modifications of the presently preferred embodiments.

We claim:

1. An optoacoustic system, comprising:
   (a) an optoacoustic transducer comprising a first array of accoustic transducers and a second array of optical fibers;
   (b) acoustic system means coupled to said first array for controllably exciting at least a first subset of said acoustic transducers to generate acoustic pulses with a prescribed pulse width, and for forming a first image based on return acoustic pulses reflected from a patient;
   (c) optical system means coupled to said second array for controllably generating optical pulses to be transmitted through at least a first subset of said optical fibers toward said patient, and for forming a second image based on light reflected from said patient; and
   (d) image correlation means for correlating said first and second images.

2. A system as recited in claim 1, wherein the same acoustic transducers are used to both transmit and receive acoustic pulses to and from said patient.

3. A system as recited in claim 1, wherein said first array comprises a plurality of ultrasonic transducers.

4. A system as recited in claim 3, wherein said ultrasonic transducers are piezoelectric transducers.

5. A system as recited in claim 1, wherein said first array is an annular array in which said acoustic transducers are arranged coaxially.

6. A system as recited in claim 5, wherein said second array comprises a circular array of optical fibers disposed around an outer periphery of said first array.

7. A system as recited in claim 5, wherein said second array comprises a circular array of optical fibers disposed around an inner periphery of said first array.

8. A system as recited in claim 7, wherein said second array further comprises a bundle of optical fibers disposed within said inner periphery.

9. A system as recited in claim 1, wherein said first and second arrays are linear arrays.

10. A system as recited in claim 1, wherein said optical system means comprises means for generating pulses of light of a plurality of wavelengths, whereby tissues having different absorption characteristics will produce image features that are distinguishable from one another.

11. A system as recited in claim 10, wherein said optical system comprises multiple lasers to produce said plurality of wavelengths.

12. A system as recited in claim 10, wherein said optical system comprises a single white light source and a chopper to produce said plurality of wavelengths.

13. A system as recited in claim 1, further comprising means for simultaneously exciting groups of at least two of said acoustic transducers.

14. A system as recited in claim 13, further comprising means for sequentially exciting different groups of said acoustic transducers.

15. A system as recited in claim 1, wherein said optical system means comprises a picosecond pulser for generating optical pulses having a pulse width in the range of about 0.01 picosecond to 100 nanoseconds.

16. A system as recited in claim 15, wherein said pulse width is in the range of about 0.1 picosecond to 10 nanoseconds.

17. A system as recited in claim 1, further comprising means for providing a beam reference and trigger signal ($LS_1'$) indicative of the timing of the optical pulses transmitted through said first subset of said optical fibers toward said patient.

18. An optoacoustic imaging method, comprising the steps of:

(a) placing an optoacoustic transducer adjacent a body part of a patient to be imaged, said optoacoustic transducer comprising a first array of acoustic transducers and a second array of optical fibers;

(b) controllably exciting at least a first subset of said acoustic transducers to generate acoustic pulses with a prescribed pulse width, and forming a first image based on return acoustic pulses reflected from a patient;

(c) controllably generating optical pulses to be transmitted through at least a first subset of said optical fibers toward said patient, and forming a second image based on light reflected from said patient; and (d) correlating said first and second images.

19. A method as recited in claim 18, wherein the same acoustic transducers are used to both transmit and receive acoustic pulses to and from said patient.

20. A method as recited in claim 18, wherein said first array comprises a plurality of ultrasonic transducers.

21. A method as recited in claim 20, wherein said ultrasonic transducers are piezoelectric transducers.

22. A method as recited in claim 18, wherein said first array is an annular array in which said acoustic transducers are arranged coaxially.

23. A method as recited in claim 22, wherein said second array comprises a circular array of optical fibers disposed around an outer periphery of said first array.

24. A method as recited in claim 22, wherein said second array comprises a circular array of optical fibers disposed around an inner periphery of said first array.

25. A method as recited in claim 24, wherein said second array further comprises a bundle of optical fibers disposed within said inner periphery.

26. A method as recited in claim 18, wherein said first and second arrays are linear arrays.

27. A method as recited in claim 18, wherein said step (c) comprises generating pulses of light of a plurality of wavelengths, whereby tissues having different absorption characteristics will produce image features that are distinguishable from one another.

28. A method as recited in claim 27, wherein multiple lasers are used to produce said plurality of wavelengths.

29. A method as recited in claim 27, a single white light source and a chopper are used to produce said plurality of wavelengths.

30. A method as recited in claim 18, wherein step (b) comprises simultaneously exciting groups of at least two of said acoustic transducers.

31. A method as recited in claim 30, further comprising sequentially exciting different groups of said acoustic transducers.

32. A method as recited in claim 18, wherein step (c) comprises the use of a picosecond pulser to generate optical pulses having a pulse width in the range of about 0.01 picosecond to 100 nanoseconds.

33. A method as recited in claim 32, wherein said pulse width is in the range of about 0.1 picosecond to 10 nanoseconds.

34. A method as recited in claim 18, further comprising providing a beam reference and trigger signal ($LS_1'$) indicative of the timing of the optical pulses transmitted through said first subset of said optical fibers toward said patient.

* * * * *